(12) United States Patent
Dahl et al.

(10) Patent No.: US 6,697,676 B2
(45) Date of Patent: Feb. 24, 2004

(54) MEDICAL ELECTRICAL LEAD HAVING AN EXPANDABLE ELECTRODE ASSEMBLY

(75) Inventors: Roger Dahl, Andover, MN (US); Duane Zytkovicz, Ham Lake, MN (US); Stephen Sundquist, Minnetonka, MN (US); Thomas M. Soukup, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 421 days.

(21) Appl. No.: 09/836,015

(22) Filed: Apr. 17, 2001

(65) Prior Publication Data

US 2002/0151949 A1 Oct. 17, 2002

Related U.S. Application Data

(60) Provisional application No. 60/257,459, filed on Dec. 21, 2000.

(51) Int. Cl.⁷ .................................................. A61N 1/04
(52) U.S. Cl. ........................................ 607/126; 600/372
(58) Field of Search ............................ 607/126, 115, 607/116, 119, 127; 600/380, 381, 373, 372

(56) References Cited

U.S. PATENT DOCUMENTS

| | | |
|---|---|---|
| 4,394,866 A | 7/1983 | Hughes |
| 4,402,328 A | 9/1983 | Doring |
| 4,402,330 A | 9/1983 | Lindemans |
| 4,454,888 A | 6/1984 | Gold |

(List continued on next page.)

FOREIGN PATENT DOCUMENTS

| | | |
|---|---|---|
| EP | 0 601 338 B1 | 10/1998 |
| WO | WO 99/11320 | 3/1999 |
| WO | WO 00/56398 | 9/2000 |
| WO | WO 00/56399 | 9/2000 |

OTHER PUBLICATIONS

U.S. patent application Ser. No. 60/254,102.
U.S. patent application Ser. No. 09/598,983.

Primary Examiner—Edward K. Look
Assistant Examiner—Thor Campbell
(74) Attorney, Agent, or Firm—Elisabeth L. Belden; Girma Wolde-Michael

(57) ABSTRACT

An implantable device including an elastically compressible member coupled to a distal end of a lead and further coupled to at least one electrode. The compressible member is in a contracted state when the electrode is being delivered to an implant site. At the implant site, the compressible member is expanded to urge the electrode into contact with tissue. Compressible member further includes a keyed structure to engage a stiffening member such as a stylet. The stiffening member is used both to deliver the electrode to the implant site, and to rotate the compressible member, if necessary, so that the electrode contacts predetermined body tissue. According to one aspect of the invention, an introducer having an inner lumen with a diameter that is smaller than that of the compressible member may be used to disengage the stiffening member from the compressible member. In one embodiment, compressible member includes a conductor wound to form multiple turns that are aligned during electrode delivery, but which expand into a non-aligned configuration after deployment. In another embodiment, compressible member includes a spring clip that has a compressed profile during delivery, and an expanded profile after deployment.

14 Claims, 9 Drawing Sheets

U.S. PATENT DOCUMENTS

| | | |
|---|---|---|
| 4,627,439 A | 12/1986 | Harris |
| 4,699,611 A | 10/1987 | Bowden |
| 5,071,407 A | 12/1991 | Termin et al. |
| 5,117,828 A * | 6/1992 | Metzger et al. ............ 600/380 |
| 5,170,802 A | 12/1992 | Mehra |
| 5,224,491 A | 7/1993 | Mehra |
| 5,246,014 A | 9/1993 | Williams et al. |
| 5,282,845 A | 2/1994 | Bush et al. |
| 5,387,233 A | 2/1995 | Alferness et al. |
| 5,423,772 A | 6/1995 | Lurie et al. |
| 5,423,878 A | 6/1995 | Franz |
| 5,531,781 A | 7/1996 | Alferness et al. |
| 5,549,109 A | 8/1996 | Samson et al. |
| 5,584,873 A | 12/1996 | Shoberg et al. |
| 5,683,445 A | 11/1997 | Swoyer |
| 5,788,715 A | 8/1998 | Watson, Jr. et al. |
| 5,845,396 A | 12/1998 | Altman et al. |
| 5,925,073 A | 7/1999 | Chastain et al. |
| 5,931,864 A | 8/1999 | Chastain et al. |
| 6,094,596 A | 7/2000 | Morgan |
| 6,129,750 A | 10/2000 | Tockman et al. |
| 6,144,882 A | 11/2000 | Sommer et al. |
| 6,161,047 A * | 12/2000 | King et al. .................. 607/62 |

* cited by examiner

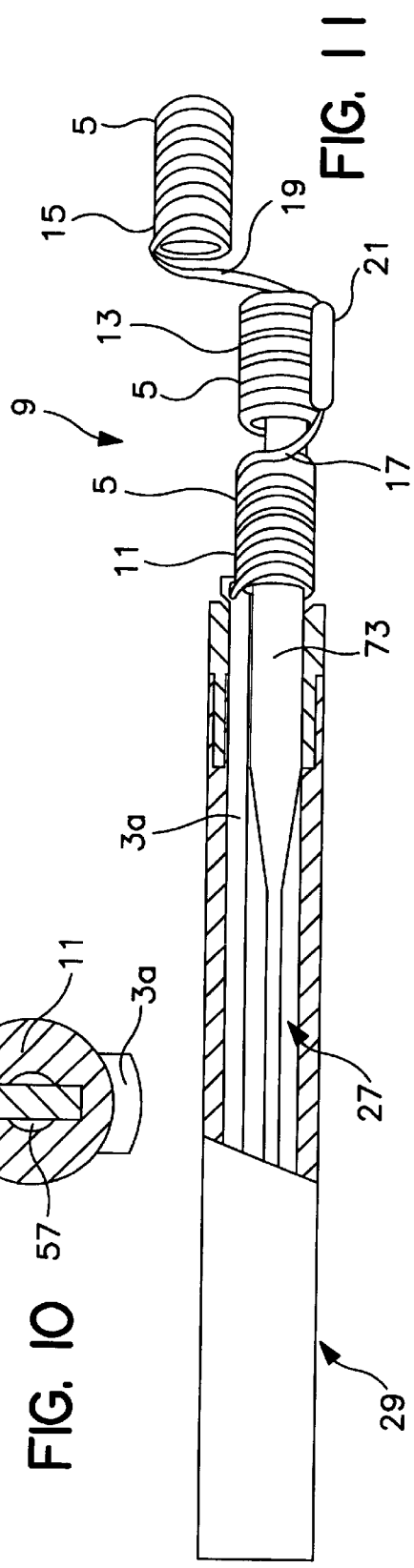

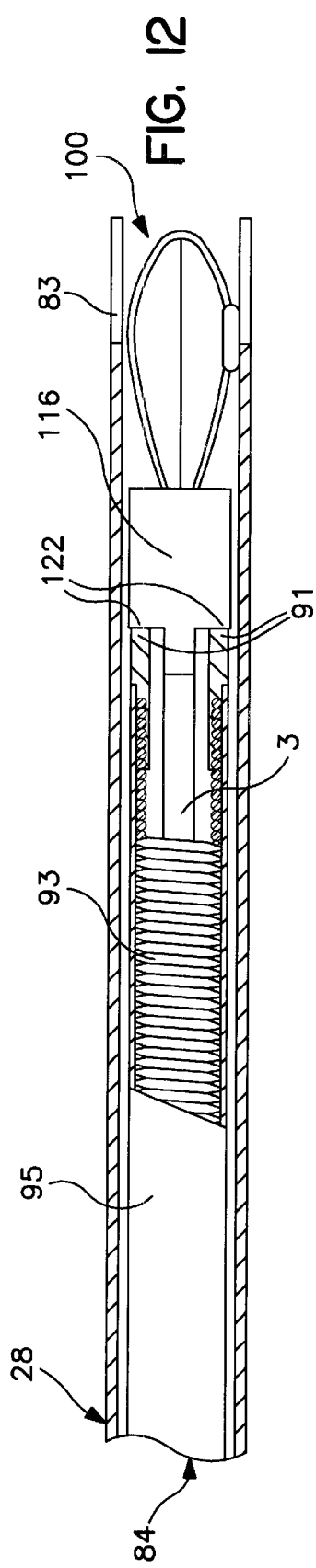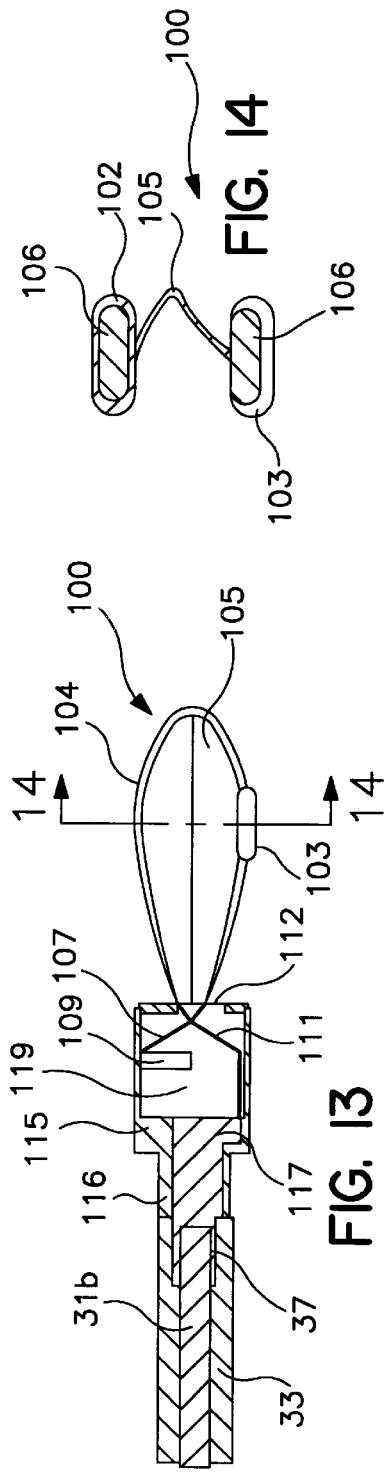

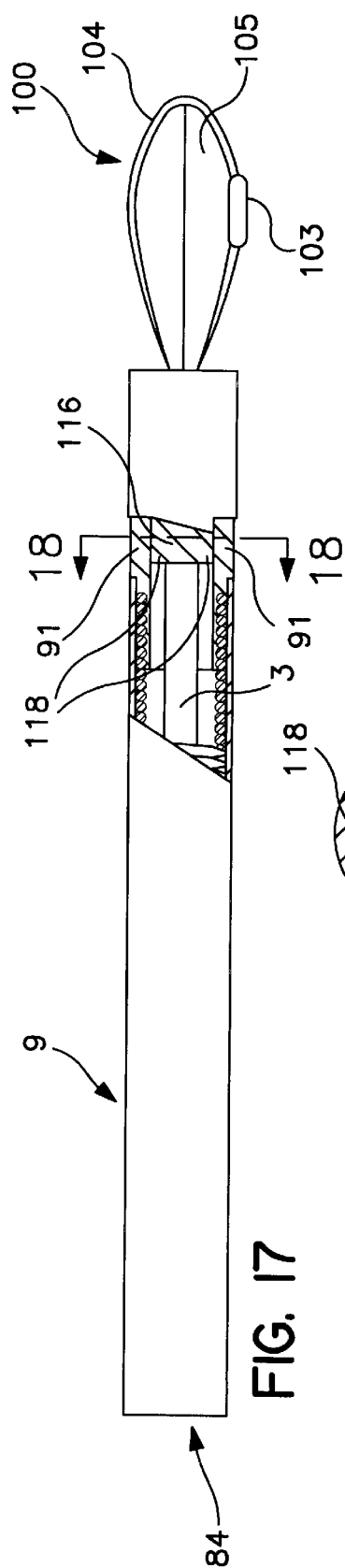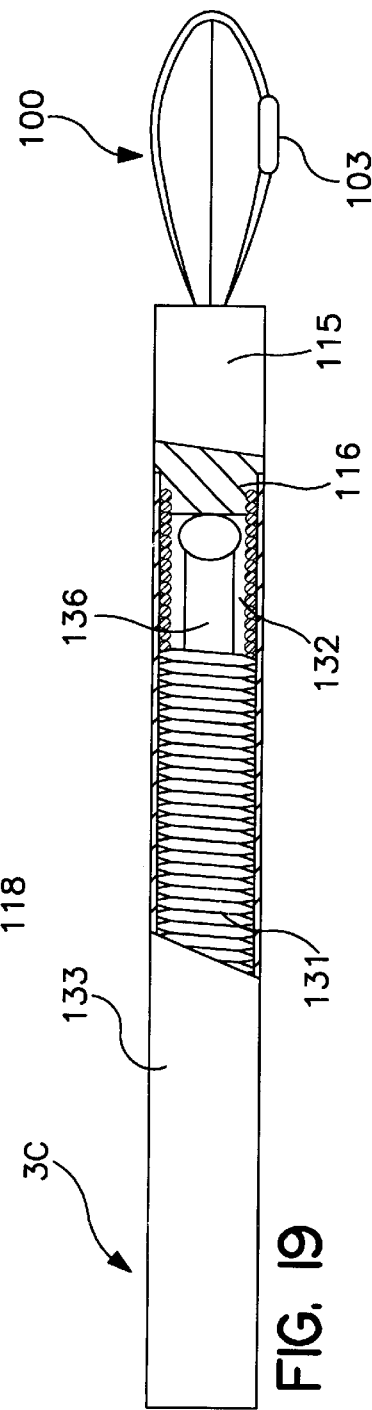

MEDICAL ELECTRICAL LEAD HAVING AN EXPANDABLE ELECTRODE ASSEMBLY

RELATED APPLICATIONS

This Application claims priority to provisionally-filed U.S. Patent Application Ser. No. 60/257,459 filed Dec. 21, 2000 entitled "Medical Electrical Lead Having An Expandable Electrode Assembly", which is incorporated herein by reference in its entirety.

FIELD OF THE INVENTION

The present invention relates to electrical medical leads generally; and, more particularly, relates to implantable cardiac pacing and defibrillation leads that include expandable electrodes.

BACKGROUND OF THE INVENTION

Over the years, numerous leads have been designed for the purpose of pacing the atria. One basic approach has been to provide the lead with a pre-formed "J"-shape, adapted to result in the electrode at the tip of the lead being reliably located in the right atrial appendage. Various approaches to providing a J-shaped lead have included the provision of molded, curved polyurethane lead bodies or sheaths as in U.S. Pat. No. 4,394,866 issued to Hughes and U.S. Pat. No. 4,627,439 issued to Harris, curved silicone rubber sheaths as in U.S. Pat. No. 4,402,328 issued to Doring, curved coils as in U.S. Pat. No. 4,402,330 issued to Lindemans, and curved reinforcing wires as in U.S. Pat. No. 4,454,888 issued to Gold. Such curve providing structures are incorporated in the distal portion of the lead so that it maintains a J-shaped configuration after implant, allowing the electrode to continue to resiliently engage the right atrial appendage until such time as it is anchored in place by means of fibrotic tissue growth.

Pacing the atria has also been accomplished by means of electrode leads located in the coronary sinus. One of the earlier coronary sinus leads is the Medtronic, Inc. Model 6992 Coronary Sinus Lead which has a generally straight lead body, carrying two ring electrodes. More recently, leads having pre-formed curved configurations have been employed for pacing and/or mapping the electrical activity of the atria, including U.S. Pat. No. 5,423,772 issued to Lurie, U.S. Pat. No. 5,387,233 issued to Alferness et al., and pending, commonly assigned U.S. Pat. No. 5,683,445 to Swoyer, incorporated herein by reference in its entirety. An additional design for a curved coronary sinus lead is disclosed in commonly assigned U.S. Pat. No. 6,144,882 to Sommer et al., also incorporated herein by reference in its entirety.

One mechanism for retaining an electrode at a desired site of implant involves use of a compression mechanism that allows the electrode to be compressed during delivery, then expanded to contact the walls of a vessel. U.S. Pat. No. 5,071,407 to Termin et al. discloses a fixation element constructed of braided, helically wound filaments that are deformed during delivery. The filaments expand to form a cylindrical structure having a radius sized to contact surrounding tissue. Similar mechanisms are disclosed in U.S. Pat. Nos. 5,224,491 and 5,170,802 to Mehra, both of which disclose an electrode having a hollow, cylindrical conductive body inserted into the vessel in which the electrode is to be located and which is expanded into contact with the interior surface of the blood vessel.

Although the prior art discloses expandable members adapted to contact tissue for purposes of delivering electrical stimulation to the heart, the problem of orienting a discrete electrode associated with an expandable member has not been addressed. The orientation of a stimulating electrode may be critical in certain instances. For example, an electrode located in a coronary vein for pacing the atrium or the left ventricle may unintentionally stimulate nerves, causing patient discomfort. One known problem is the stimulation of the phrenic nerve by a pacing electrode placed in a posterior lateral vein. To prevent this stimulation from occurring, the surface of an electrode should be oriented toward, and make intimate contact with, the epicardial surface of the heart. The problem can be further reduced by ensuring that the surface area of the electrode is appropriate for the intended use. A large electrode surface not only wastes energy, but also increases the likelihood that unwanted nervous stimulation may occur.

What is needed, therefore, is an improved electrode assembly that may be oriented within the vasculature so that stimulation is directed to a predetermined target location, and unwanted stimulation is avoided.

SUMMARY OF THE INVENTION

The present invention includes an elastically compressible member at a distal end of a lead. During the implantation process, the compressible member is in a contracted state. After being delivered to the implant site and deployed, the compressible member expands, and is positively affixed within a cardiac vein or coronary artery. Compressible member includes at least one electrode that is urged into contact with tissue when the compressible member expands. Compressible member further includes a keyed structure designed to engage a stiffening member. The stiffening member is used both to deliver the compressible member to the implant site, and to rotate the compressible member, if necessary, so that the electrode contacts predetermined body tissue, and undesirable stimulation of muscle or other tissue is avoided.

In one embodiment, compressible member includes a conductor wound to form multiple turns. When the compressible member is deployed, stiffening member engages compressible member to cause all of the multiple turns to be substantially aligned. After deployment, however, at least one of the multiple turns moves out of alignment with other ones of the multiple turns so that compressible member has an enlarged profile sized to contact the walls of a cardiac vein or coronary artery.

In another embodiment, compressible member includes a spring clip that has a compressed profile during delivery, and an expanded profile after deployment. The spring clip defines an inner region, which in one embodiment, retains a flexible membrane-like structure adapted to prevent tissue in-growth to the spring clip.

In each of the embodiments, the electrode assemblies contain spring members that can be elastically deformed to reduce the outside diameter of said assemblies to facilitate insertion and delivery to the implant site. Each electrode assembly is attached to an elongated lead body comprised of a conductor and insulation and adaptable for coupling to an electrical pulse generator.

As mentioned above, compressible member further includes a key structure designed to engage a stiffening member. The stiffening member may be a bladed stylet, for example, having a distal end designed to be inserted within a slot of the compressible member. By rotating the proximal end of the stylet, the at least one electrode of the compressible member may be placed in a predetermined orientation in a vessel.

According to yet another aspect of the invention, an introducer may be provided having an inner lumen to receive the lead when the compressible member is coupled to the stylet. The outer diameter of the introducer is smaller than the compressible member so that when the introducer is slid distally, force asserted by the distal end of the introducer on the compressible member disengages the compressible member from the stylet.

In one embodiment of the invention, lead includes a lumen to receive the stylet. In another embodiment, the lead is coupled to the compressible member in an offset manner such that the longitudinal axis of the lead and the compressible member are not aligned. This allows a proximal end of the style to be located adjacent the lead body while the distal end of the stylet engages the compressible member.

According to one method of using the present invention, a guide catheter is navigated to a desired site of implant. The lead is coupled to stiffening member and loaded into the introducer. The introducer is then used to advance the lead within the lumen of the guide catheter. The introducer is used to deploy the compressible member, which may include rotating the compressible member to orient the electrode in a particular location. If the electrode requires re-positioning, the stylet may be re-inserted into the compressible member. When the electrode is in the desired location, the introducer and stiffening member are withdrawn from the body. Finally, the guide catheter is withdrawn from the body.

According to another method of using the invention, a lead including a lumen is loaded with stiffening member. Then the lead is loaded into the introducer. The introducer is used to push the compressible member to the implant site. The compressible member is deployed, and the introducer and stiffening member are withdrawn from the body.

Other scopes and aspects of the invention will become apparent to those skilled in the art from the detailed description and the accompanying drawings.

BRIEF DESCRIPTION OF THE DRAWINGS

FIG. 7 a plan view of a bladed stylet as may be used with the current invention.

FIG. 9 is a plan view of another embodiment of lead 1 that may be used in conjunction with the current invention, and further illustrates bladed stylet engaging the lumens of housing members of the electrode assembly.

FIG. 10 is a cross-sectional view of the electrode assembly at line 10—10 of FIG. 9, and illustrates a bladed stylet inserted into a keyed channel of the electrode assembly.

FIG. 11 is a side cutaway view of the electrode assembly as it is being deployed.

FIG. 12 illustrates a second embodiment of an expanding electrode assembly that is compressed within a delivery catheter.

FIG. 13 is a side cutaway view of the electrode assembly of FIG. 12.

FIG. 14 is a cross-sectional view of the electrode assembly at line 14—14 of FIG. 13.

FIG. 17 is a side cutaway view of one embodiment of the electrode assembly of FIGS. 12 and 13 including keyed extensions.

FIG. 18 is a cross-sectional view of the assembly of FIG. 17 at line 18—18.

FIG. 19 is a side cutaway view of yet another embodiment of the lead body that will allow delivery of the electrode assembly without the use of an introducer.

DETAILED DESCRIPTION OF THE DRAWINGS

Figure 1:
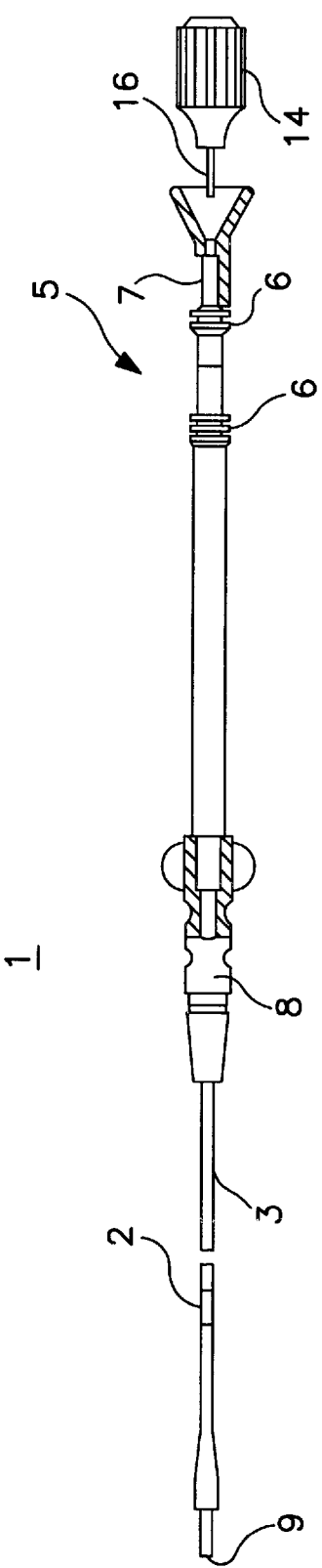
FIG. 1 is an exemplary lead that may be used in conjunction with the current invention.

FIG. 1 is a plan view of one embodiment of a lead that may be used in conjunction with the present invention. Lead 1 comprises an elongate lead body 3 and a tip electrode assembly, designated generally by reference numeral 9 in FIG. 1, disposed at the distal section of lead body 3. Distal section of lead body may further include a ring electrode 2. Lead body 1 is covered by an insulative sleeve of flexible biocompatible and biostable insulating material, such as polyurethane or silicone rubber. At the proximal end of lead 1, a terminal assembly designated generally as 5 is provided for coupling lead 1 to an implantable pulse generator (not shown). Terminal assembly 5 is provided with sealing rings 6 and a terminal pin 7, all of a type known in the art. An anchoring sleeve 8 may also be provided on lead body 3. As would be familiar to those of ordinary skill in the art, anchoring sleeve 8 slides over lead body 3 and serves as a point for suturing lead body 3 to body tissue at the insertion point of lead 1 in a fashion known in the art. Anchoring sleeve 8 and terminal assembly 5 are preferably fabricated from silicone rubber, although they may also be constructed of any other suitable biocompatible material known in the art.

Lead 1 as shown in FIG. 1 may also include an adapter 9 for coupling to terminal pin 7. Adapter may serve as a stylet guide for stylet assembly 14 that is required to impart stiffness to lead 1 during the implantation procedure. Stylet assembly includes a stylet body 16 that is received within an inner lumen (not shown in FIG. 1) of the lead as a stiffening member to aid in lead placement. Adapter 9 and stylet assembly 14 are discarded after use and before connection of terminal pin 7 to a pacemaker pulse generator.

Figure 2:
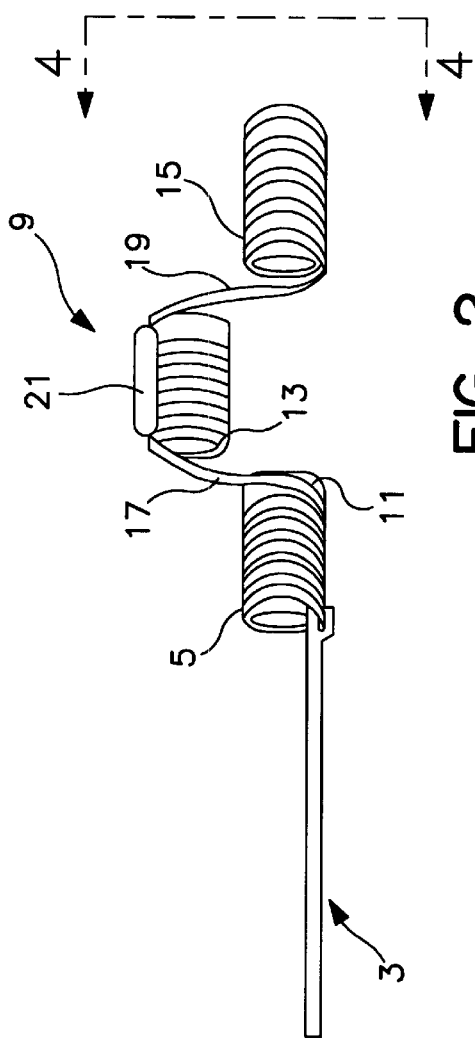
FIG. 2 is a plan view illustrating one embodiment of the electrode assembly of the current invention.

FIG. 2 is a plan view of the distal end of a lead body 3, including one embodiment of the electrode assembly 9. In this embodiment, a conductive element 5 such as a wire forms three sets of offset turns. Each set of turns surrounds a respective insulative housing member, including housing members 11, 13, and 15. Insulative housing member 11 is most proximal, housing member 13 is intermediate the other housing members, and housing member 15 is most distally located. Each of the housing members may be formed of a bio-compatible insulative material such as silicone or a suitable polymer as is known in the art. For example, insulative housing members 11–15 may be formed from a rigid polymer such as a 75D durometer polyurethane. In one embodiment, the diameter of the housing members may having an outer diameter ranging from approximately 0.040" to 0.060", and a length ranging from 0.08" to 0.09".

Housing member 13 is coupled to an electrode 21, as will be discussed further below. The electrode 21 may be of any electrode configuration known in the art. According to one aspect of the invention, the electrode is comprised of platinum-iridium alloy with a sintered and platinized surface and in one form of this embodiment its surface area may range from approximately 3 mm$^2$ to 6 mm$^2$.

As stated previously, conductive element 5 forms three sets of turns surrounding the three insulative housing members. Conductive element 5 further includes transition region 17 between the first and second set of turns, and transition region 19 between the second and third set of turns. When the electrode assembly is in the deployed state, the transition regions 17 and 19 are not compressed, as shown in FIG. 2.

It will be appreciated by one skilled in the art that the electrode assembly 9 of FIG. 2 may include more than three sets of turns. Moreover, each of the sets of turns may include as few as a single turn, or more than the number of turns illustrated in FIG. 2.

Figure 3:
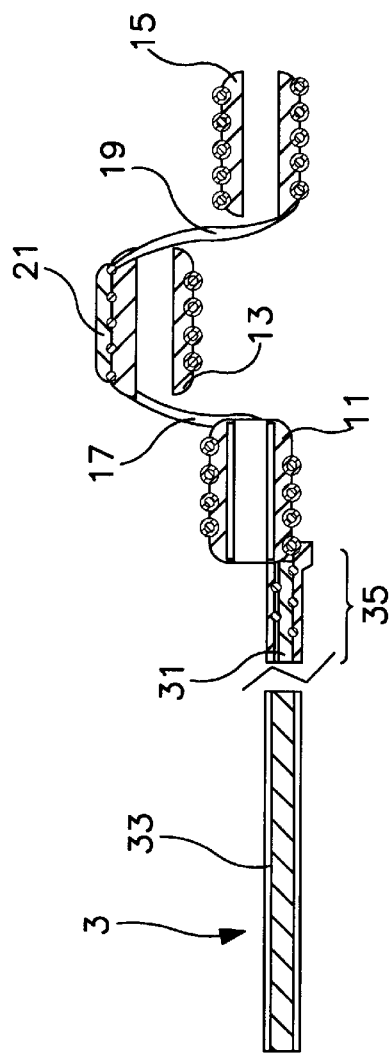
FIG. 3 is a cutaway view of the lead of FIG. 2.

FIG. 3 is a side cutaway view of electrode assembly 9 of FIG. 2. This view shows a cross-sectional view of conductive member 5, which is comprised of a spring wire 51 surrounded by an insulating coating 53. Spring wire 51 may be formed of any type of conductive material, and in one embodiment is comprised of stainless steel with a diameter ranging from approximately 0.005" to 0.007". Insulating coating 53 may be a fluoropolymer with a thickness ranging from approximately 0.003" to 0.005".

Spring wire 51 is electrically coupled to electrode 21, and is also electrically coupled to a conductor 31 carried by lead body 3. In FIG. 3, spring wire 51 is shown coiled around distal end 32 of conductor 31. However, spring wire could be coupled to the conductor in other ways, as be soldering, welding, brazing, or by using a crimp sleeve. Conductive member 31 extends to the proximal end of lead body and couples electrode 21 via spring wire 51 to connector pin 7 of FIG. 1.

Lead body 3 further includes lumen 20 to receive a stiffening member such as a stylet. The stiffening member is adapted to extend beyond the distal end of lead body 3 and engage housing members 11, 13, and 15 via the inner lumens of these housing members in a manner to be discussed further below. Lead body 3 further includes an outer jacket 22, and an inner insulative tubing member 23, also to be discussed below.

Figure 4:
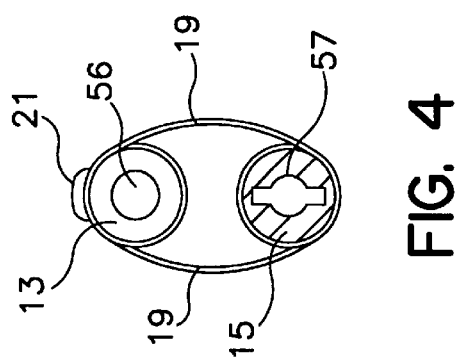
FIG. 4 is a cross-sectional end view at line 4—4 of FIG. 2.

FIG. 4 is a cross-sectional end view of electrode assembly 9 at line 4—4 of FIG. 2. This view shows the most distal housing member 15 coupled to the intermediate housing member 13 via transition region 19 of conductive member 5. Electrode 21 is electrically and mechanically coupled to conductive member 5 as, for example, with a welding, soldering, brazing, or crimping process. Electrode is also mechanically coupled to insulative housing member 13 via a bio-compatible adhesive as is known in the art.

Housing members 13 and 15 include lumens 56 and 57, respectively. Lumen 57 is illustrated in FIG. 4 as having a coupling interface such as a keyed channel adapted to receive a bladed end of a stylet in a manner to be discussed further below. In one embodiment, only housing member 11 includes such a keyed channel to be used in a manner to be discussed below. In another embodiment, additional ones of the housing members 13 and 15 may include keyed channels.

The deployed electrode assembly 9 forms an elliptical arrangement and, in one form of this embodiment, the major axis of the ellipse that encompasses this section may range from approximately 0.100"–0.150" while its minor axis may range from approximately 0.050"–0.080".

Figure 5:
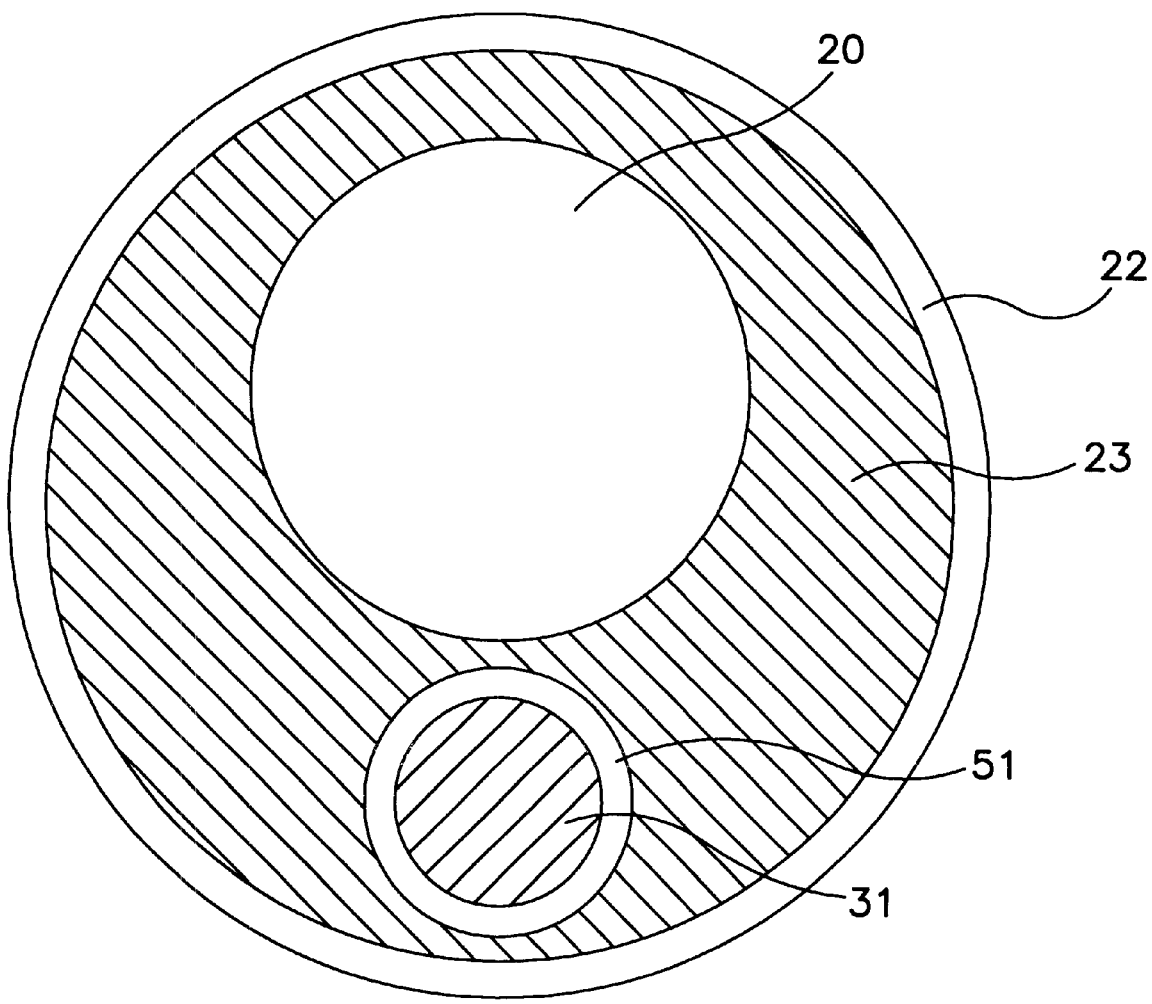
FIG. 5 is a plan view of a bladed stylet for use with the electrode assembly of FIG. 2.

FIG. 5 is a cross-sectional view of one embodiment of the lead body 3 of FIG. 3. Lead body includes jacket 22, which may be formed of a silicone or polymer. In one embodiment, jacket 22 is a polyurethane. Lead body further includes tubular member 23 that surrounds lumen 20, and also surrounds conductor 51 and spring wire 51. Tubular member is also formed of an insulating material such as a polymer that is less stiff than the material that forms jacket 22. In a preferred embodiment, tubular member is formed of silicon. FIG. 5 further shows conductor 31 being encircled by coils of spring wire 51 to form an electrical connection. As discussed above, the connection may further be enhanced by a welding, soldering, brazing or other suitable process.

Conductor 51 may take the form of either stranded or cabled conductors, as described in U.S. Pat. No. 5,584,873 issued to Shoberg, et al. incorporated herein by reference. A stranded design adaptable for use with the current invention corresponds to that disclosed in U.S. Pat. No. 5,246,014 issued to Williams et al, also incorporated herein by reference in its entirety. Other conductor types may of course also be employed, including twenty-strand cables, as described in U.S. Pat. No. 5,845,396 issued to Altman et al, also incorporated herein by reference in its entirety. In still other embodiments, the individual conductors may simply take the form of a single filar wire conductor, wound around the core member of the lead body. The lead may alternatively including multiple conductors separated by insulative strands or tubes and wound around a generally cylindrical or tubular, insulative core member, as described in commonly-assigned application entitled "Electrically-Isolated Multiple Conductor Lead Body", Ser. No. 09/598,983, filed Jun. 21, 2000, and incorporated herein by reference.

Figure 6:
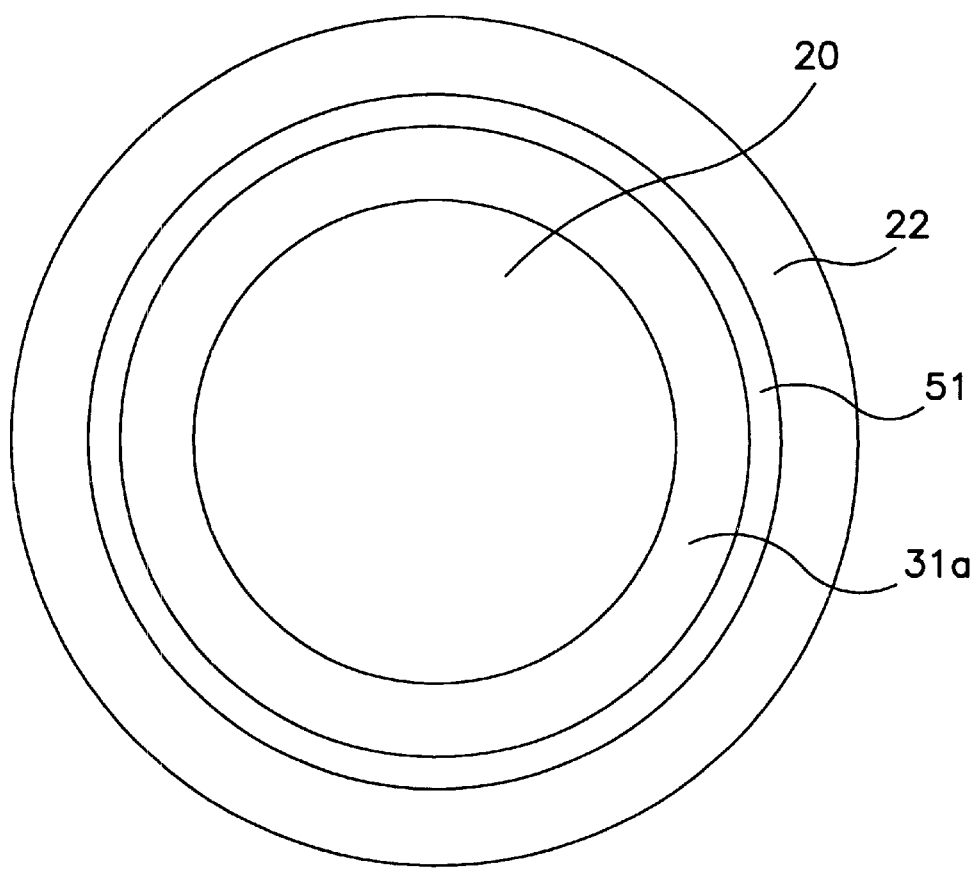
FIG. 6 is a cross-sectional view of another embodiment of lead body that may be employed by the current invention.

FIG. 6 is a cross-sectional view of another embodiment of lead body that may be employed by the current invention. In this embodiment, insulative jacket 22 surrounds conductor 31a, which in this case is a coiled conductor extending to the proximal end of the lead body. Coiled conductor 31a is also surrounded by, and electrically coupled to, spring wire 51. Coiled conductor 31a defines lumen 20, which may further be coated with a lubricious coating such as Teflon or ETFE to aid in advancing a stiffening member down the length of the lead, as will be discussed below. The lead body 3 of the current invention as shown in either FIGS. 5 and 6 may have a diameter ranging from approximately 0.020"–0.050".

FIG. 7 a plan view of a stylet 27 as may be used with the current invention. The distal end 73 of the stylet is bladed to interface with keyed channel 57 of one or more of the housing members.

Figure 8:
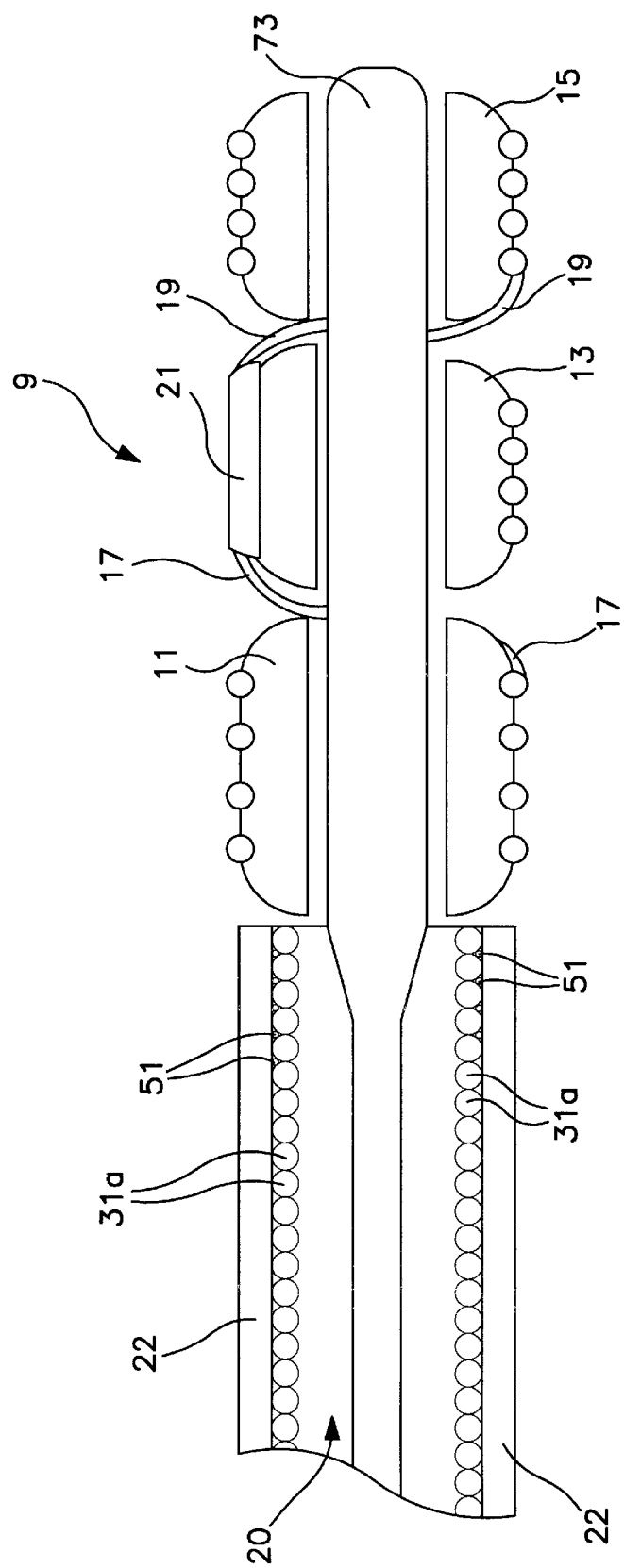
FIG. 8 is a cutaway side view of bladed stylet inserted in a lead having the lead body configuration shown in FIG. 6.

FIG. 8 is a cutaway side view of bladed stylet 27 inserted in a lead having the lead body configuration shown in FIG. 6. In this embodiment, stylet 27 is inserted in lumen 20 of lead body 3. Distal end 73 of bladed stylet extends to couple with lumens of housing members 11, 13, and 15. At least one of the housing members includes a keyed channel (not shown in FIG. 8) that engages bladed stylet so that the electrode assembly 9 may be rotated by the stylet to position electrode 21 toward the myocardium to achieve selective and efficient cardiac stimulation. When the housing members 11, 13, and 15 are in the aligned configuration shown in FIG. 8, the transition regions 17 and 19 of the spring wire 51 are elastically deformed, and under tension.

FIG. 9 is a plan view of another embodiment of a lead that may be used in conjunction with the current invention, and further illustrates bladed stylet 27 engaging the lumens of housing members 11, 13, and 15. In this view, lead body 3a does not include inner lumen 20 for receiving the stylet. Instead, lead body 3a is coupled to electrode assembly 9 in an offset manner so that the lumens of housing members 11, 13, and 15 are not longitudinally aligned with lead body 3. The proximal portion 28 of style 27 is positioned adjacent lead body 3a when distal bladed end 73 of stylet engages the electrode assembly 9.

The lead illustrated in FIG. 9 may be constructed to have a smaller lead body than the alternative lead embodiments discussed above, since the lead body 3 a does not require an inner lumen adapted to receive the bladed stylet. In this configuration, lead body 3a may have an outer diameter as small as 0.010". Lead body 3a includes a conductor (not shown in FIG. 9) that may be of any of the embodiments discussed above with respect to FIGS. 3 through 6.

FIG. 10 is a cross-sectional view of housing member 11 at line 10—10 of FIG. 9 illustrating the distal end 73 of stylet 27 inserted into keyed channel 57, and further showing the lead embodiment illustrated in FIG. 9.

FIG. 11 is a side cutaway view of the electrode assembly 9 as it is being deployed. The stylet 27 and lead body 3a are shown within an introducer 29. This introducer may be of any of the configurations known in the art for placing leads within coronary arteries or cardiac veins. In one embodiment of the inventive system, the inner diameter of the distal end of the introducer is smaller than the outer diameter of the proximal end of the electrode assembly 9. By sliding the introducer 29 forward such that the distal end of the introducer 29 asserts force against housing member 11, the electrode assembly 9 may be deployed from the end of the stylet. Such a means for dispatching electrode assemblies is disclosed in provisionally filed U.S. Patent Application No. 60/254,102 entitled "System and Method for Placing a Medical Electrical Lead" filed Dec. 8, 2000, and which is incorporated herein by reference in its entirety.

As shown in FIG. 11, the second transition region 19 of conductive member 5 decompresses when housing member 15 is deployed from the constraint of the stylet 27. This causes housing member 15 to assume a position that is not longitudinally aligned with the housing member 15. When the stylet is further decoupled from housing members 11 and 13, the first transition region 17 of conductive member 5 will also decompress so that electrode assembly 9 assumes the non-aligned configuration shown in FIG. 3.

FIG. 12 illustrates a second embodiment of an expanding electrode assembly 100 that is compressed within a delivery catheter 28. Delivery catheter may be of any construction known in the art, and may include a radiopaque marker 83 on the distal tip to serve as a reference for positioning electrode assembly 100 within the delivery catheter.

Electrode assembly 100, which is in the form of a spring clip, has a proximal end structure 116 having shoulder members 122. Proximal end structure 116 is further coupled to lead body 3b, which may be any of the lead embodiments discussed above. Electrode assembly 100 is shown loaded into an introducer 84 such that shoulder members 122 abut against the distal end 91 of introducer 84. According to this embodiment, introducer 84 may be used to advance and rotate the electrode assembly within the delivery catheter 28. The body of the introducer may be composed of a coil 93 that is coated with a flexible polymer 95. Additional details for an introducer of this embodiment are provided in provisionally filed U.S. Patent Application No. 60/254,102 entitled "System and Method for Placing a Medical Electrical Lead" referenced above.

FIG. 13 is a side cutaway view of electrode assembly 100 of FIG. 12. The electrode assembly is composed of a flat spring wire 104 that is terminated in an insulated housing 115. The ends of the wire 107 and 111 pass through an orifice 112 of the housing into cavity 119. The unconstrained end of the wire 107 is terminated with an enlarged member 109 that will prevent end 107 from exiting the orifice 112. The constrained end of the wire 111 is stripped of insulation at its proximal end and terminated within the housing by attachment to a conductive element 117 that electrically couples spring wire 104 to the lead body conductor 31b. In this embodiment, the lead conductor 31b is shown as a cable crimped within a ring 37 that protrudes from the proximal end 116 of the housing 115 and is in electrical connection with the constrained end of the clip wire 111 via the conductive element 117. The outer insulation 33 of the lead body 3 extends over the junction at the ring 37. In one form of this embodiment the lead body 3 diameter may range from approximately 0.025"–0.050" and the conductor diameter may range from approximately 0.006"–0.015".

As noted above, the external portion of the spring wire forms a clip. An electrode 103 is mechanically and electrically coupled to spring wire. The electrode 103 may be of any electrode configuration known in the art. In one embodiment, electrode 103 is comprised of a platinum-iridium alloy with a sintered and platinized surface and, in one form of this embodiment, its surface area may range from approximately 3 mm$^2$ to 6 mm$^2$. Shown spanning the inside portion of the clip of electrode assembly 100 is a polymer film 105 that may be integrated into one embodiment of this assembly in order to prevent tissue in-growth through the center of the implanted assembly.

FIG. 14 is a cross-sectional view of the electrode assembly of FIG. 13 at line 14—14. This view shows a cross-section of flat spring wire 104, which includes a generally flattened conductor 106 that may be composed of a stainless steel. Flattened conductor 106 is coated with a biocompatible insulating material 102 that may be a fluoropolymer. In one form of this embodiment, the width of the wire 104 may range from approximately 0.010"–0.020" and its thickness from approximately 0.003"–0.010". The wall thickness of the insulating coating 102 may range from approximately 0.003"–0.010". This view further illustrates the manner in which film 105 is folded when the clip mechanism of electrode assembly 100 is in the compressed state.

Figure 15:
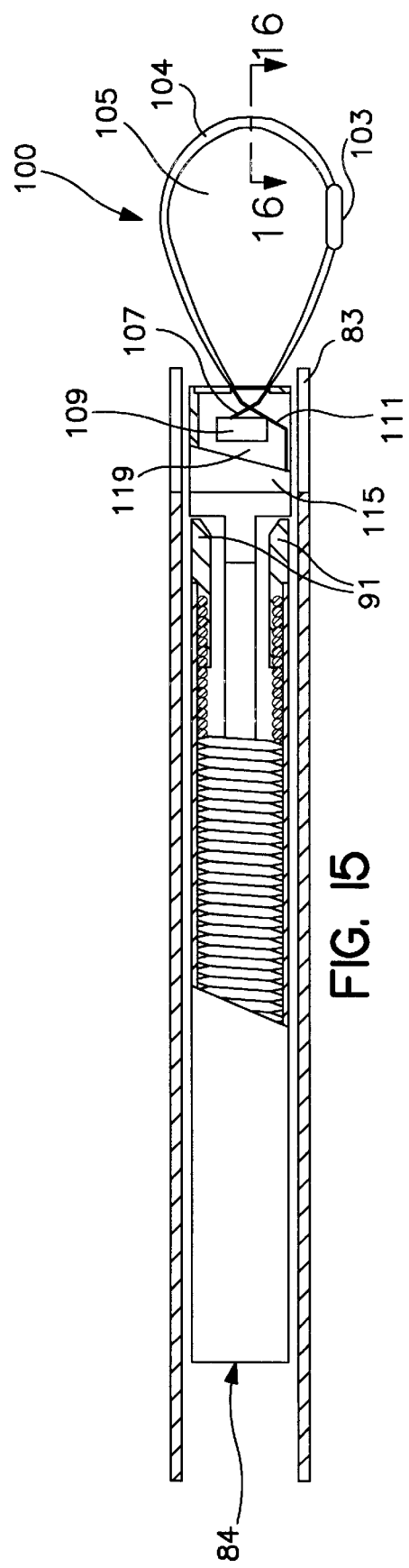
FIG. 15 is a side cutaway view of the electrode assembly of FIGS. 12 and 13 as it is being deployed by the introducer

FIG. 15 is a side cutaway view of the electrode assembly of FIGS. 12 and 13 as it is being deployed by the introducer 84. The radiopaque marker 83 at the distal end of the delivery catheter 28 serves to indicate the relative position of the electrode 103 as the assembly 100 is being pushed out of the catheter. As electrode assembly 100 is deployed the assembly expands, and the unconstrained end of the wire 107 moves toward the center of the cavity 119. In one form of this embodiment, the expanded width of the clip 101 may range from approximately 0.04" to 0.16".

Figure 16:
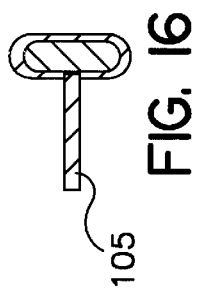
FIG. 16 is a cross-sectional view of the film included within the electrode assembly at line 16—16 of FIG. 15.

FIG. 16 is a cross-sectional view of the film included within the electrode assembly 100 at line 16—16 of FIG. 15. This figure illustrates the manner in which the film 105 is taunt when electrode assembly 100 is expanded.

FIG. 17 is a side cutaway view of one embodiment of the electrode assembly 100 positioned between the distal tip 91 of the introducer 84 wherein the proximal end 116 of the insulative housing 115 includes a keyed structure having keyed extensions 118 that are not longitudinally aligned with lead body 3. Use of keyed extensions 118 are discussed further below.

FIG. 18 is a cross-sectional view of the assembly of FIG. 17 at line 18—18. This view shows one embodiment of the proximal end 116 of housing 115 wherein keyed extensions 118 are shown interfacing with the mating interior of the distal tip of the introducer 91. This mating mechanism allows the introducer to transfer torque to the assembly for positioning of the electrode 103.

FIG. 19 is a side cutaway view of yet another embodiment of the lead body 3c that will allow delivery of the electrode assembly 100 without the use of an introducer. In this embodiment the lead conductor is a coil 131 having a central lumen 132 to accommodate a stiffening stylet 136. A tubing 133 that may be polyurethane or silicone forms the outer insulation around the coil. The coil conductor 131 may be joined with a crimp or weld to the proximal end 116 of the housing 115. In this embodiment, an introducer is not necessary because the stylet 136 may serve to stiffen the lead body so that it may be pushed through the delivery catheter. Coil conductor 131 provides the necessary torsional stiffness so that the lead body 3c may transfer torque to the electrode assembly 100 in order to orient the electrode 103. In one form of this embodiment the lead body diameter may range from 0.04"–0.09".

Variations and modifications to the present invention may be possible given the above disclosure. However, all such variations and modifications are intended to be within the scope of the invention claimed by this letters patent.

In conjunction with the above disclosure, we claim:

What is claimed is:

1. A medical device to be implanted in a body, comprising:
    a lead body including a longitudinal axis;
    a compressible member coupled to the end of the lead body, the compressible member including a keyed structure and a longitudinal axis not aligned with the longitudinal axis of the lead body;
    an electrode coupled to the compressible member, and
    a stiffening member adapted to engage the keyed structure to allow the compressible member to be rotated so that the electrode is in a predetermined orientation in the body.

2. The device of claim 1, and further including an introducer having a proximal end, a distal end, and an inner lumen to receive the lead body, the distal end having an inner diameter smaller than the compressible member, and whereby the distal end of the introducer is adapted to disengage stiffening member from the keyed structure of the compressible member.

3. The device of claim 2, wherein the stiffening member is a stylet.

4. The device of claim 3, wherein the stylet is a bladed stylet and the keyed structure is a keyed lumen shaped to receive the bladed style.

5. The device of claim 3, wherein the lead body includes a lumen to receive the stylet.

6. The device of claim 1, and further including a guide catheter having an inner lumen to receive the introducer loaded with the lead body, the guide catherer being capable of navigating within the body to a predetermined implant site.

7. A medical device to be implanted in a body comprising:
    a lead body:
    a compressible member coupled to the end of the lead body, the compressible member including a keyed structure;
    an electrode coupled to the compressible member; and
    a stiffening member adapted to engage the keyed structure to allow the compressible member to be rotated so that the electrode is in a predetermined orientation in the body;
    wherein the compressible member includes a conductor wound in multiple coils, wherein the multiple coils are substantially longitudinally aligned prior to deployment, and wherein upon deployment, at least one of the coils is adapted to decompress to a non-aligned position as compared to at least one other one of the multiple coils.

8. The device of claim 7, wherein the conductor is a spring wire.

9. A method of placing a medical electrical lead within a body, comprising the methods of:
    a.) providing, at a distal end of the medical electrical lead, a compressible electrode assembly having a coupling interface and a conductor wound to include multiple coils;
    b.) engaging a stiffening member with the coupling interface;
    c.) orientating the electrode assembly in a predetermined position within the body; and
    d.) disengaging the stiffening member from the coupling interface.

10. The method of claim 9, wherein step b.) includes the step of engaging the stiffening member such that all of the multiple coils of the conductor are substantially aligned along a longitudinal axis.

11. The method of claim 10, wherein step d.) includes the step of disengaging the stiffening member to cause at least one of the multiple coils of the conductor to move into a position that is not in alignment with others of the multiple coils.

12. The method of claim 9, wherein step d.) includes the step of providing an introducer having a distal end adapted to couple to the compressible electrode assembly when the stiffening member is engaging the coupling interface, the distal end of the introducer further adapted to assert force on the compressible electrode assembly to cause the compressible electrode assembly to disengage from the stiffening member.

13. The method of claim 12, wherein step c.) includes the methods of
    navigating a guide catheter having an inner lumen to a predetermined implant site in the body; and
    utilizing the stiffening member to advance the electrode assembly within the inner lumen of the guide catheter to the predetermined implant site in the body.

14. A medical device to be implanted in a body, comprising:
    a lead body including an insulated housing coupled to a distal end of the lead body;
    a compressible member comprising a flat spring wire formed in a loop extending distally from the lead body, the wire including a first end and a second end held within the insulated housing; and
    an electrode coupled to the loop portion of the compressible member;
    wherein the first end of the wire is unconstrained within the housing allowing compression of the loop portion of the compressible member.

* * * * *